United States Patent
Rodriguez et al.

(10) Patent No.: US 9,320,611 B2
(45) Date of Patent: Apr. 26, 2016

(54) SURGICALLY IMPLANTABLE JOINT SPACER

(71) Applicants: Carlos Andres Rodriguez, Coconut Creek, FL (US); Cira Rodriguez, Miami, FL (US)

(72) Inventors: Carlos Andres Rodriguez, Coconut Creek, FL (US); Cira Rodriguez, Miami, FL (US)

(*) Notice: Subject to any disclaimer, the term of this patent is extended or adjusted under 35 U.S.C. 154(b) by 343 days.

(21) Appl. No.: 13/943,333

(22) Filed: Jul. 16, 2013

(65) Prior Publication Data

US 2014/0114424 A1 Apr. 24, 2014

Related U.S. Application Data

(60) Provisional application No. 61/716,534, filed on Oct. 20, 2012.

(51) Int. Cl.
*A61F 2/30* (2006.01)
*A61F 2/44* (2006.01)
*A61F 2/46* (2006.01)

(52) U.S. Cl.
CPC .............. *A61F 2/442* (2013.01); *A61F 2/4465* (2013.01); *A61F 2/4611* (2013.01); *A61F 2002/30092* (2013.01); *A61F 2002/30125* (2013.01); *A61F 2002/30556* (2013.01); *A61F 2002/30579* (2013.01); *A61F 2002/30777* (2013.01); *A61F 2002/30797* (2013.01)

(58) Field of Classification Search
CPC .. A61F 2/44; A61F 2/4455; A61F 2002/4495
USPC .......................................... 623/17.13, 17.16
See application file for complete search history.

(56) References Cited

U.S. PATENT DOCUMENTS

| 5,059,193 | A | * | 10/1991 | Kuslich | ................. | F16B 13/061 606/247 |
| 5,171,278 | A | * | 12/1992 | Pisharodi | .............. | A61F 2/4455 128/898 |
| 5,693,100 | A | * | 12/1997 | Pisharodi | .............. | A61F 2/4455 623/17.16 |
| 5,800,526 | A | * | 9/1998 | Anderson | ................. | A61F 2/07 606/191 |
| 6,395,035 | B2 | * | 5/2002 | Bresina et al. | .......... | A61F 2/442 606/247 |
| 6,595,998 | B2 | | 7/2003 | Johnson et al. | | |

(Continued)

FOREIGN PATENT DOCUMENTS

EP 1 259 179 11/2002
EP 1 928 332 6/2008

(Continued)

*Primary Examiner* — Zade Coley
(74) *Attorney, Agent, or Firm* — Allen D. Hertz, P.A.; Allen D. Hertz

(57) ABSTRACT

A spacer formed of an intermetallic compound, such as nitinol. The spacer includes two segments shaped in opposing arches. The unique properties of the intermetallic compound enable the material to be deformed into a planar, insertable shape when the material is cooled below a transition temperature and returns to the undeformed shape when the material returns to an ambient, operational temperature. An expansion mechanism assembly can engage with the spacer to apply an expansion force. The expansion force extends the spacer longitudinally drawing the spacer into the planar configuration. The expansion mechanism assembly can be used to guide the spacer into the desired position within the patient. The spacer control mechanism assembly is subsequently removed, relieving the expansion force. The spacer returns to the natural undeformed shape as it returns to body temperature. Retention features can be integrated in the spacer to aid in retaining the spacer in location.

20 Claims, 10 Drawing Sheets

(56) References Cited

U.S. PATENT DOCUMENTS

| | | | |
|---|---|---|---|
| 7,070,598 B2 * | 7/2006 | Lim | A61B 17/025 606/99 |
| 7,166,131 B2 | 1/2007 | Studer et al. | |
| 7,238,186 B2 * | 7/2007 | Zdeblick | A61B 17/1671 623/17.11 |
| 7,645,301 B2 * | 1/2010 | Hudgins | A61F 2/441 623/17.11 |
| 7,666,226 B2 | 2/2010 | Schaller | |
| 7,758,647 B2 | 7/2010 | Arnin et al. | |
| 7,857,857 B2 * | 12/2010 | Kim | A61F 2/442 623/17.11 |
| 7,955,384 B2 * | 6/2011 | Rafiee et al. | A61F 2/2451 623/2.11 |
| 7,959,652 B2 * | 6/2011 | Zucherman et al. | A61B 17/7068 606/249 |
| 8,097,018 B2 * | 1/2012 | Malandain | A61B 17/025 606/246 |
| 8,231,639 B2 | 7/2012 | Bolduc et al. | |
| 8,231,678 B2 | 7/2012 | Lambrecht | |
| 8,236,055 B2 | 8/2012 | Cordaro | |
| 8,439,972 B2 * | 5/2013 | Badawi | A61F 9/00781 604/8 |
| 8,529,628 B2 * | 9/2013 | Marino | A61B 17/7098 623/17.11 |
| 8,778,027 B2 * | 7/2014 | Medina | A61F 2/4455 623/17.16 |
| 2006/0282166 A1 | 12/2006 | Molz et al. | |
| 2006/0293753 A1 | 12/2006 | Thramann | |
| 2008/0140203 A1 | 6/2008 | Davis | |
| 2008/0281364 A1 | 11/2008 | Chirico et al. | |
| 2009/0012564 A1 | 1/2009 | Chirico et al. | |
| 2009/0118836 A1 * | 5/2009 | Cordaro | A61F 2/4455 623/17.16 |
| 2009/0163918 A1 * | 6/2009 | Levy et al. | A61B 17/8858 606/63 |
| 2009/0204216 A1 | 8/2009 | Biedermann et al. | |
| 2010/0063548 A1 | 3/2010 | Wang | |
| 2010/0228289 A1 | 9/2010 | Park | |
| 2011/0004308 A1 | 1/2011 | Marino et al. | |
| 2011/0054538 A1 | 3/2011 | Zehavi et al. | |
| 2011/0093075 A1 | 4/2011 | Duplessis et al. | |
| 2011/0245926 A1 | 10/2011 | Kitchen | |
| 2012/0116520 A1 | 5/2012 | Cauthen, III et al. | |

FOREIGN PATENT DOCUMENTS

| | | |
|---|---|---|
| WO | WO 2005/097006 | 10/2005 |
| WO | WO 2007/002602 | 1/2007 |
| WO | WO 2007/117908 | 10/2007 |
| WO | WO 2008/022206 | 2/2008 |

* cited by examiner

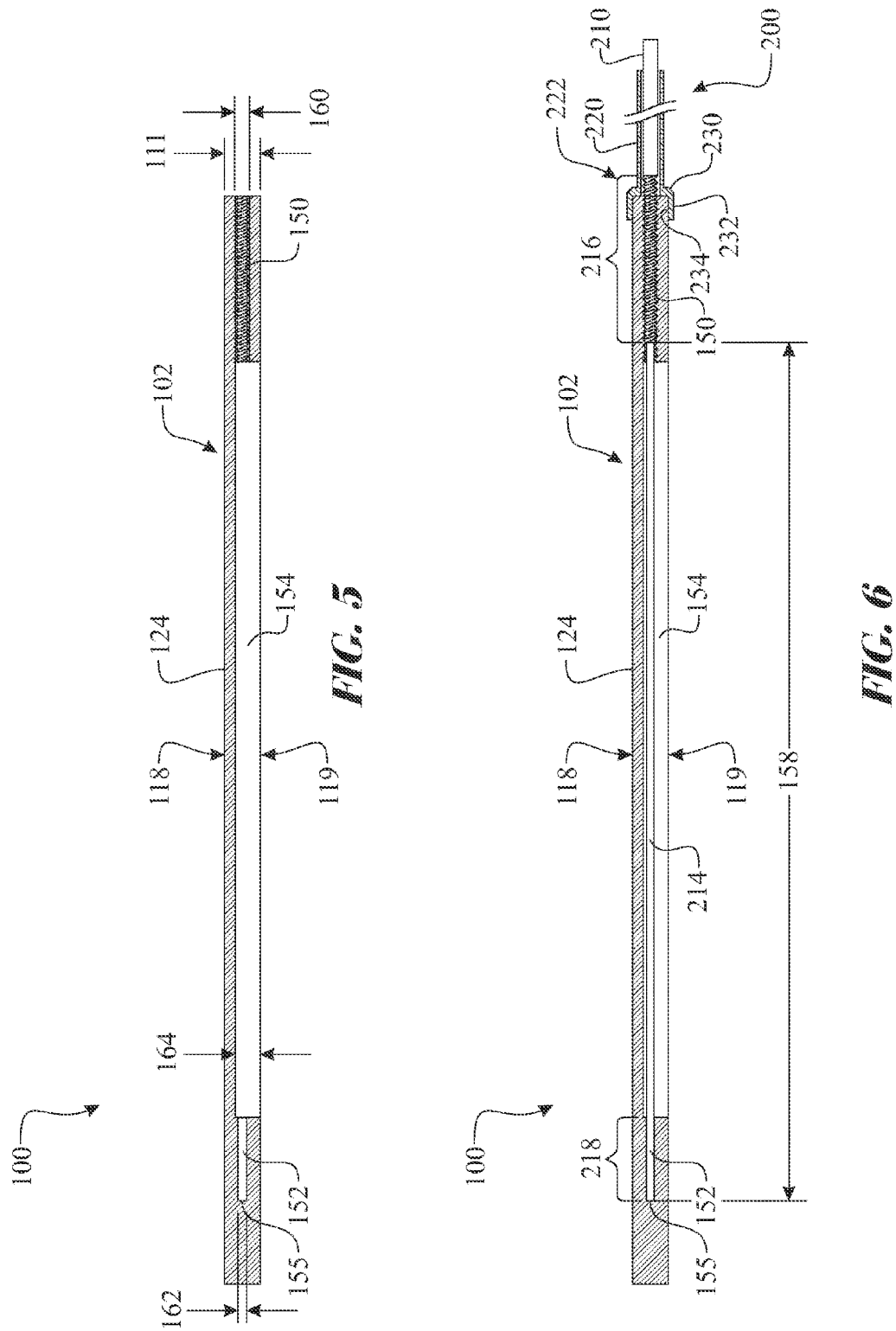

SURGICALLY IMPLANTABLE JOINT SPACER

CROSS-REFERENCE TO RELATED APPLICATION

This Non-Provisional Utility application claims the benefit of U.S. Provisional Patent Application Ser. No. 61/716,534, filed on Nov. 15, 2012, which is incorporated herein in its entirety.

FIELD OF THE INVENTION

The present disclosure generally relates to a medically implanted spacer. More particularly, the present disclosure relates to a medically implanted spacer for insertion within a joint formed between two adjacent bones to enhance movement or fuse in a deteriorated biological joint.

BACKGROUND OF THE INVENTION

Biological joints can degrade over time, deteriorate as a result of a birth defect or a disease, become damaged as a result of an accident or unwarranted motion, malformations due to incorrect growths, and the like. As the joint deviates from a normal, mobile condition, the malformed joint can cause multiple issues to the individual or animal, including sporadic or constant pain, limited motion, any degree of incapacitation, and the like.

Common joints that require surgical attention include inter-vertebrae discs, hips, knees, shoulders, elbows, and the like.

Inter-vertebrae discs can degrade over time or become damaged where they no longer function properly. The defective inter-vertebrae discs allow unwarranted motion between two adjacent vertebrae. The defective inter-vertebrae discs limit or reduce the support along the individual's spine. Over time, the defective inter-vertebrae disc needs surgical attention. Inter-vertebrae discs are addressed by fusing two or more adjacent vertebrae together. One short-term drawback of this procedure is the resulting limitation of motion incurred by the individual. A long-term drawback is that over time, the fused region increases stresses on adjacent joints, resulting in additional surgical procedures to fuse other regions of the individual's spine.

Other joints, such as hips and shoulders, are commonly formed having a first end of one bone moveably engaged with a mating end of a mating bone. Most joints comprise a first joint member formed in a ball and the mating joint member formed in a socket. As either or both of the surfaces of the joint members wears or deteriorates, the support of the joint degrades, hindering the mobility of the individual. In addition to the reduced mobility, the deteriorating joint can cause inflammation, discomfort, and other unwanted physical and psychological issues.

A few material compositions are known that have a unique property, a reversible, solid-state phase transformation known as a martensitic transformation. One of these material compositions is Nickel titanium, also known as nitinol. Nitinol is a metal alloy of nickel and titanium, where the two elements are present in roughly equal atomic percentages.

Nitinol alloys exhibit two closely related and unique properties: shape memory and superelasticity (also called pseudoelasticity). Shape memory refers to the ability of nitinol to undergo deformation at one temperature, and then recover its original, undeformed shape upon heating above its "transformation temperature". Superelasticity occurs at a narrow temperature range below its transformation temperature; in this case, no heating is necessary to cause the undeformed shape to recover, and the material exhibits enormous elasticity, some 10-30 times that of ordinary metal. The elasticity commonly occurs at a lower temperature, where the material recovers to its original shape upon returning to an ambient temperature.

Nitinol has an additional benefit, where the material is conducive to medical applications. The material can be surgically implanted into a patient with very limited risk of biological rejection.

Therefore, what is desired is a device capable of being surgically implanted to repair or overcome medial deficiencies of a damaged or defective biological joint.

SUMMARY OF THE INVENTION

The present disclosure is generally directed to a surgically implanted spacer for use in a joint formed between adjoining ends of two bones.

In a first aspect, the surgically implantable spacer may include:

a spacer member formed of a material having martensitic properties;

a pair of segment defining slots formed through the spacer member, each slot routed longitudinally, extending from a location proximate a first end of the spacer member to a location proximate a second end of the spacer member, each slot being located between a centerline and a respective edge of the spacer member;

the pair of slots segmenting the spacer member into a circumferentially located, implanted spacer peripheral segment and a centrally located implanted spacer inner segment;

a threaded shaping passage extending inward from the first spacer member end oriented along a spacer member longitudinal centerline;

a blind receptacle in linear alignment with the threaded shaping passage initiating at a blind receptacle orifice and extending towards the second spacer member end;

wherein the spacer member is shaped into an undeformed, operating temperature configuration having the implanted spacer peripheral segment forming an arch in a first direction and the implanted spacer inner segment forming an arch in a first direction, wherein the first direction is opposite of the second direction.

In a second aspect, the arches of the surgically implantable spacer are straightened with an insertion of a spacer shaping control rod, wherein a threaded segment of the spacer control rod engages with the threaded shaping passage and an extension segment of the spacer control rod engages with a distal end of the blind receptacle.

In another aspect, the straightening process is enhanced by reducing the temperature of the spacer member to a temperature that is below a transformation temperature.

In another aspect, the spacer shaping control rod is inserted through a spacer control sleeve.

In another aspect, a spacer torsional control element is affixed to the spacer control sleeve. The spacer torsional control element comprises at least one spacer torsional control section having a spacer torsional control surface, wherein the spacer torsional control surface engages with a surface of the spacer member.

In another aspect, the spacer torsional control element comprises a pair of spacer torsional control sections, each section having a spacer torsional control surface, wherein the spacer torsional control surface engages with a respective surface of the spacer member.

In another aspect, an interior surface of the blind receptacle is smooth.

In another aspect, the spacer member further comprises a spacer control rod clearance slot formed in one side thereof, the spacer control rod clearance slot spanning between the threaded shaping passage and the blind receptacle.

In another aspect, the spacer member is shaped in an oblong oval shape.

In another aspect, each segment defining slot is shaped having an arch, the arch having a radial center located on side of the longitudinal axis that is opposite of the slot.

In another aspect, the spacer member further comprises a slot stress relief formed at each end of the segment-defining slot. The slot stress relief is preferably formed as a circular hole.

In another aspect, the spacer member further comprises at least one retention feature. The retention feature can be a tab that is cut, shaped and formed from the material of the spacer member.

In another aspect, the spacer member further comprises a series of retention features located along the circumferential outer edge.

In another aspect, the spacer member further comprises a series of retention features located along the circumferential inner edge.

In another aspect, the spacer member further comprises a series of retention features located along the circumferential edge of the inner segment.

In another aspect, the retention features are oriented extending outward when the spacer member is placed into an undeformed, operating temperature configuration.

In another aspect, the spacer shaping control rod is inserted through a spacer control sleeve.

In another aspect, the surgically implantable spacer is inserted between two adjacent vertebrae.

In another aspect, the surgically implantable spacer is inserted within one of: a hip joint, a shoulder joint, a knee, an elbow, and the like.

In another aspect, the spacer member is fabricated of a planar sheet of material.

In another aspect, the spacer member is fabricated of a planar sheet of material having a thickness providing suitable rigidity for the target application.

In another aspect, the operational segment of the spacer expansion control assembly has a diameter suitable for the application. In one exemplary embodiment, the diameter of the segment is smaller than the thickness of the spacer member.

In another aspect, the spacer member is fabricated of a planar sheet of material having a thickness up to 12 mm, with a preferred thickness of up to 9 mm.

In another aspect, the spacer member is fabricated of a planar sheet of material having a thickness of between 3 mm and 12 mm, with a preferred thickness of between 3 mm and 9 mm.

In another aspect, the spacer member is fabricated of a planar sheet of material having a thickness of between 5 mm and 12 mm, with a preferred thickness of between 5 mm and 9 mm.

In another aspect, the threaded shaping passage has a diameter of approximately 3 mm.

In another aspect, the blind receptacle has a diameter of approximately 2 mm.

In another aspect, the spacer control rod clearance slot extends inward from a bottom surface of the spacer member. The spacer control rod clearance slot would have a depth suitable to accommodate the operational segment of the spacer expansion control assembly. For example, where the operational segment of the spacer expansion control assembly has a diameter of 3 mm, the spacer control rod clearance slot would have a depth of approximately 5 mm.

In another aspect, a spacer insertion end of the spacer member is shaped to provide a circumferential edge that broadens as it extends from the spacer insertion end. The shape of the spacer insertion end provides a lead in to aid in an insertion process.

In another aspect, the spacer member is fabricated of a material considered to have a more complicated monoclinic crystal structure known as martensite at lower temperatures.

In another aspect, the spacer member is fabricated of nitinol.

In another aspect, the present invention discloses a method of use, the method comprising steps of:

obtaining a surgically implantable spacer;

reducing a temperature of the surgically implantable spacer to a temperature below the transformation temperature wherein the material becomes super-elastic;

extending the surgically implantable spacer into a planar shape by applying an extending force to the surgically implantable spacer;

inserting the surgically implantable spacer into a biological joint;

removing the extending force from the surgically implantable spacer; and warming the spacer to a temperature above the transformation temperature, wherein the material returns to its undeformed shape.

In another aspect, the process further comprises a step of retaining the surgically implantable spacer in position by including at least one retention feature.

In another aspect, the process continues by grafting material through any of a series of features of the surgically implantable spacer.

In another aspect, the surgically implantable spacer can be used in non-joint medical applications wherein the spacer is implanted in an application where the change in shape due to the nature of the material provides an advantage. Examples include aiding in healing a fracture, reshaping a curved region, where the insertion is linear (such as a nasal implant), and the like.

These and other aspects, features, and advantages of the present invention will become more readily apparent from the attached drawings and the detailed description of the preferred embodiments, which follow.

BRIEF DESCRIPTION OF THE DRAWINGS

The invention will now be described, by way of example, with reference to the accompanying drawings, in which:

FIG. 5 presents a sectioned elevation view of the surgically implantable spacer, the section being taken along section line 5-5 of FIG. 1;

FIG. 6 presents a sectioned elevation view of the surgically implantable spacer, the section being taken along section line 5-5 of FIG. 1, the illustration further comprising the spacer control mechanism assembly to show the interaction therebetween;

Like reference numerals refer to like parts throughout the several views of the drawings.

DETAILED DESCRIPTION OF THE INVENTION

Figure 1:
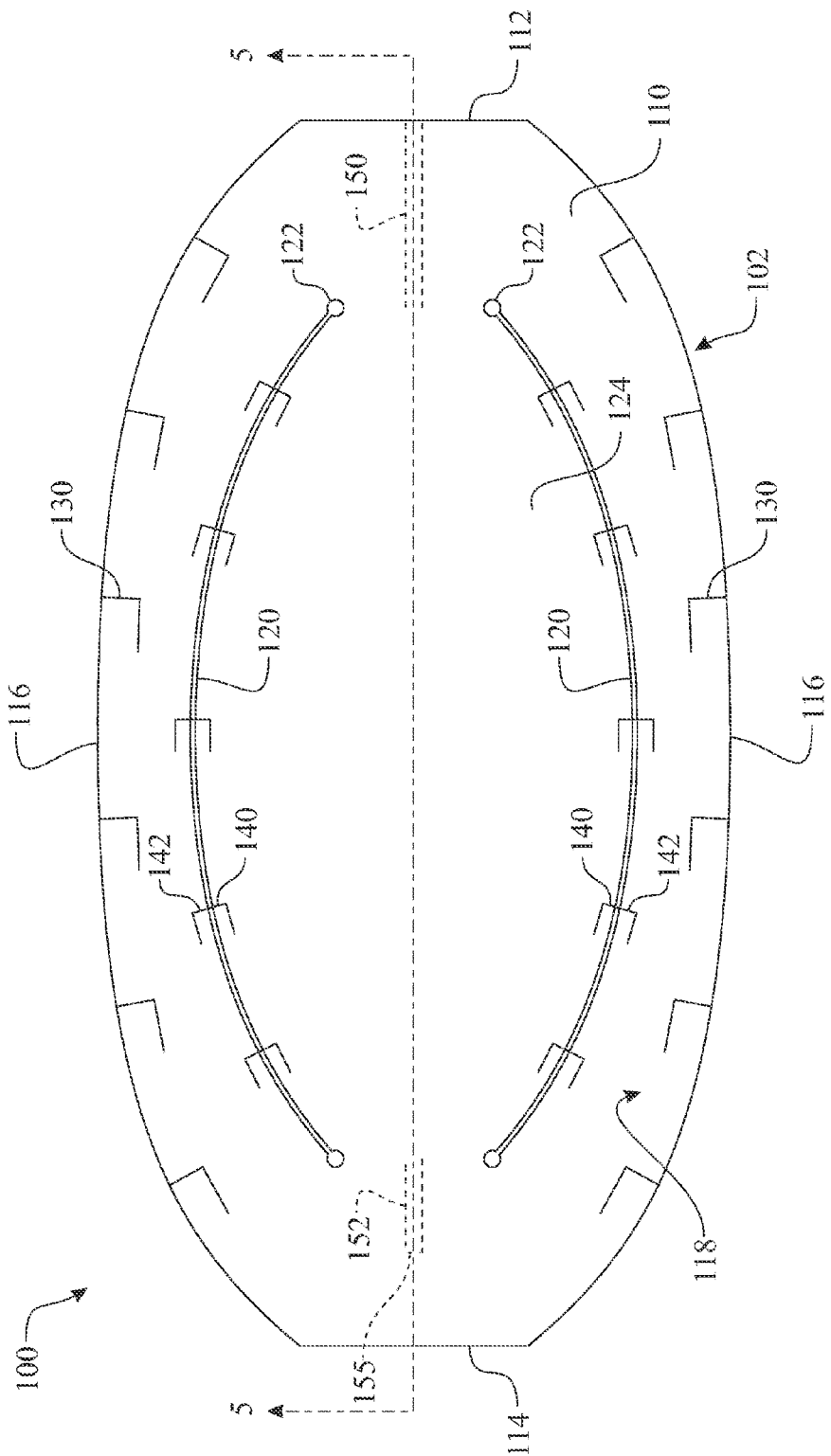
FIG. 1 presents a top view of an exemplary surgically implantable spacer, the surgically implantable spacer being shown in a super-elastic state and in a planar configuration.
Figure 2:
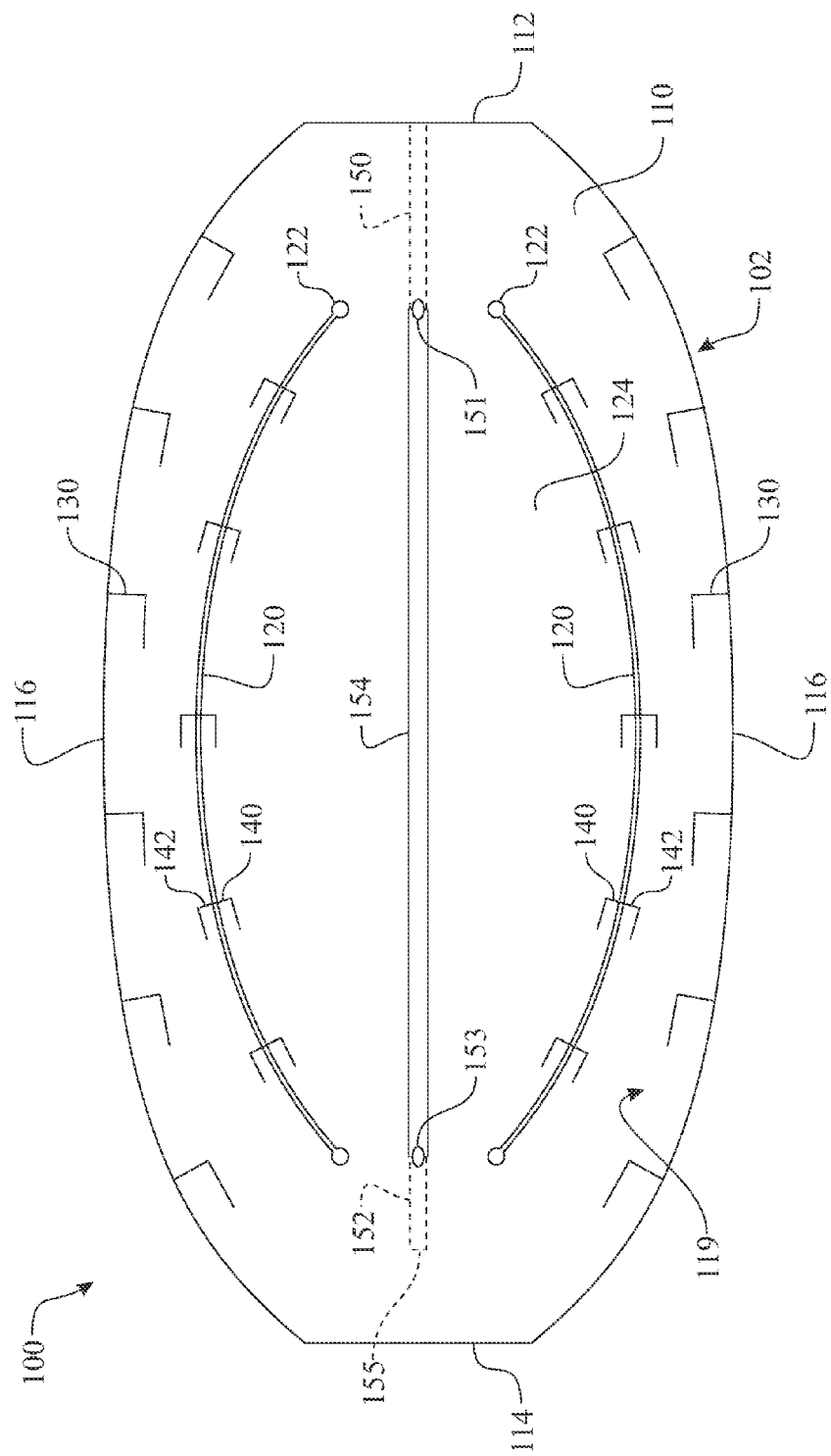
FIG. 2 presents a bottom view of the surgically implantable spacer originally introduced in FIG. 1.
Figure 3:
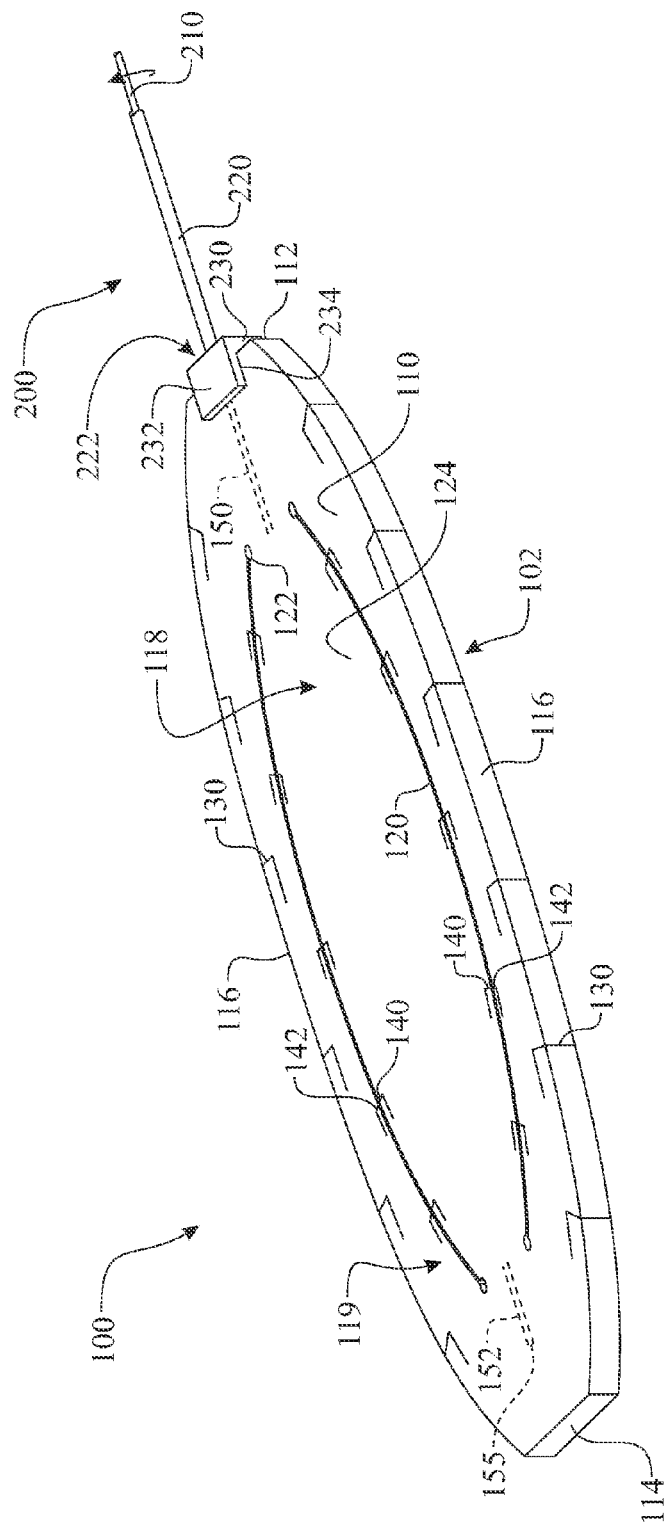
FIG. 3 presents an isometric top view of the surgically implantable spacer originally introduced in FIG. 1, the illustration introduces a spacer control mechanism assembly.
Figure 4:
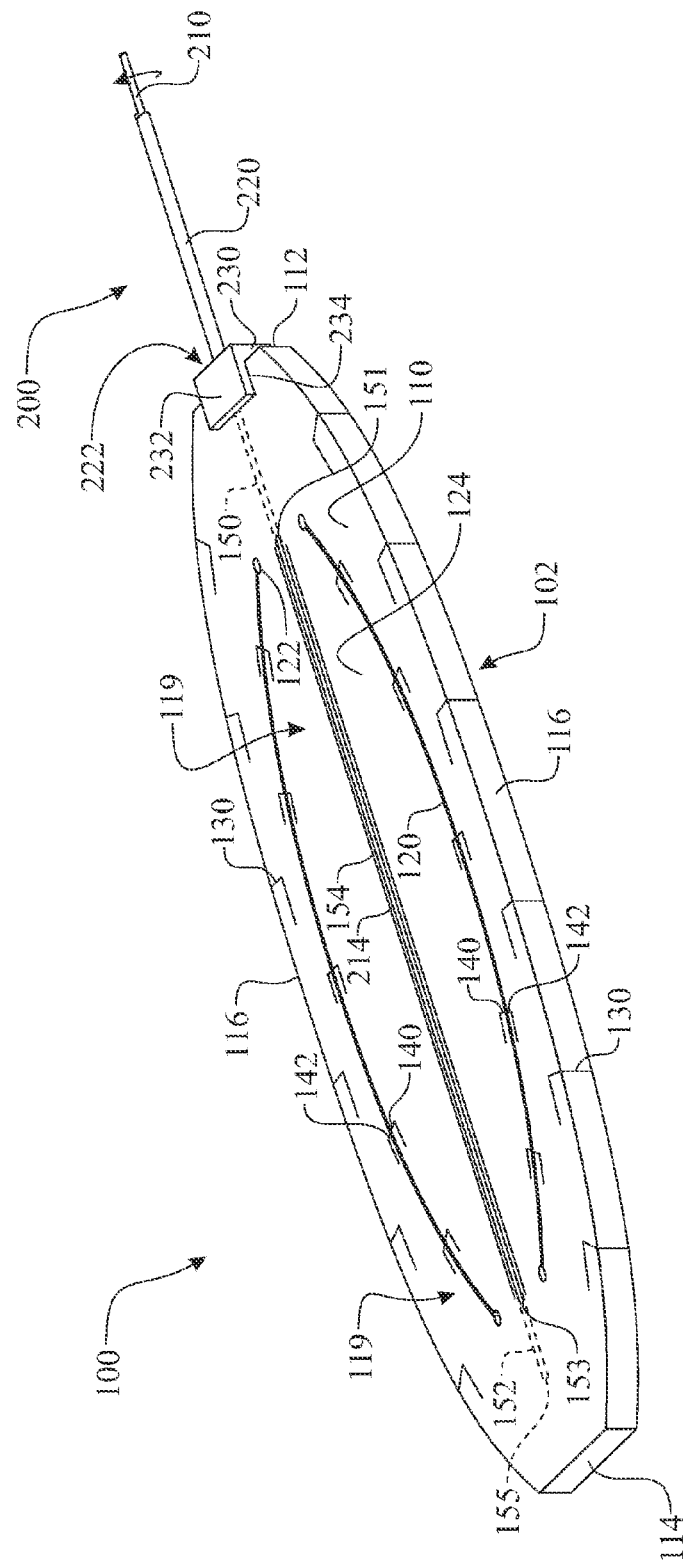
FIG. 4 presents an isometric bottom view of the surgically implantable spacer in a configuration as previously shown in FIG. 3.
Figure 7:
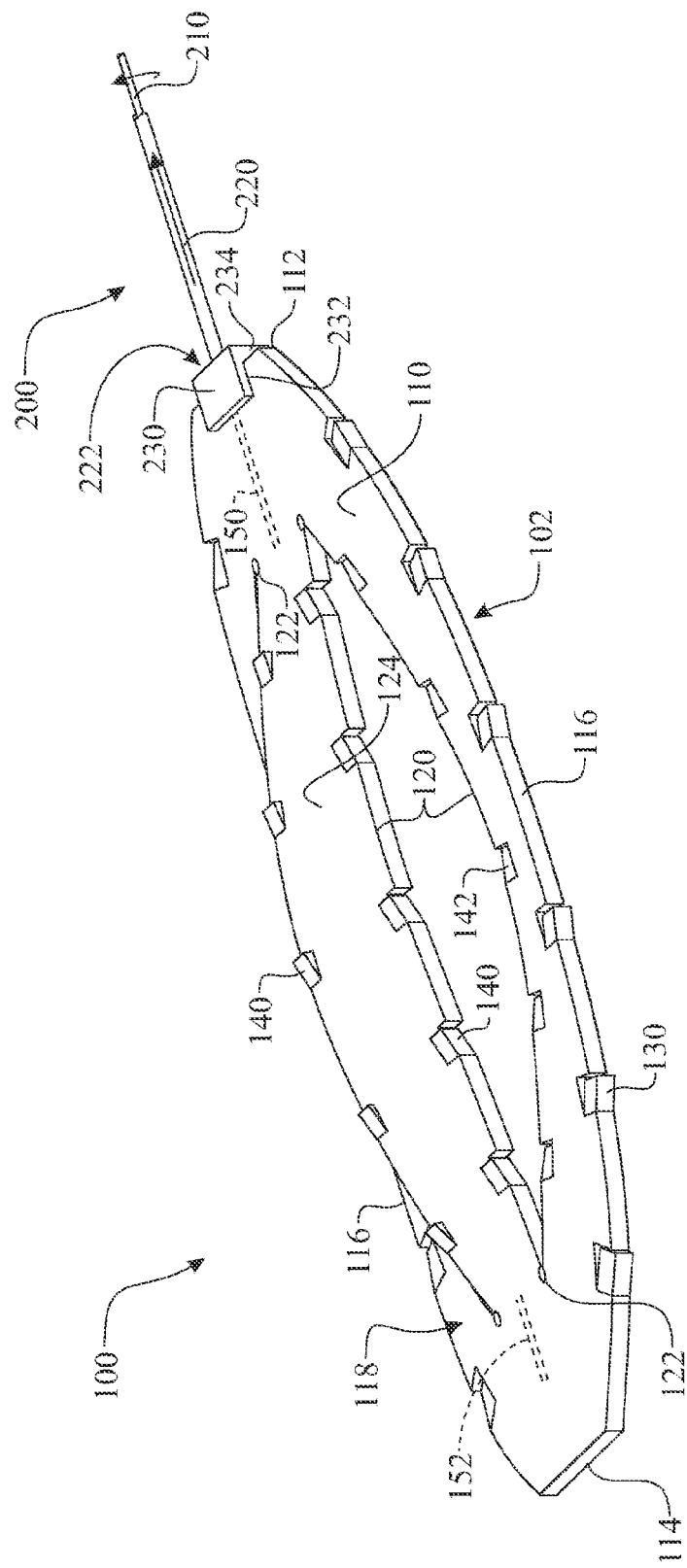
FIG. 7 presents an isometric top view of the surgically implantable spacer, the surgically implantable spacer being shown removing a shaping force and returning to an undeformed shape.
Figure 8:
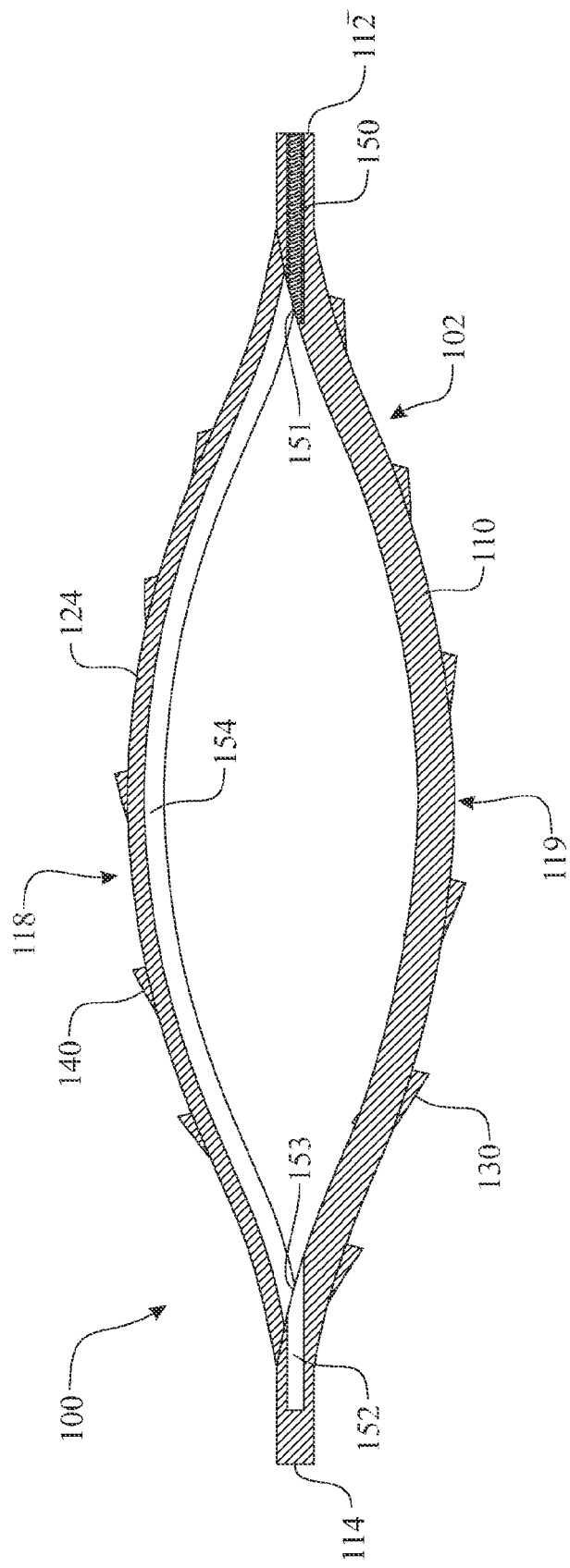
FIG. 8 presents an sectioned elevation view of the surgically implantable spacer, the surgically implantable spacer being shown in the undeformed shape.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The present disclosure is generally directed to a surgically implantable spacer 100 as illustrated in FIGS. 1 through 8. In some applications, the surgically implantable spacer 100 can be more specifically referred to as a surgically implantable disc 100. It is noted that the thickness and at least a portion of the features and shapes presented in the figures are exaggerated for clarity. The surgically implantable spacer 100 is preferably shaped from a planar sheet of raw material. The material can be any biologically acceptable material, preferably of one that has a unique property, which is a reversible, solid-state phase transformation known as a martensitic transformation. The surgically implantable spacer 100 can be provided in any suitable shape, with the preferred shape being illustrated in the respective figures and described herein. The surgically implantable spacer 100 is shaped having a peripheral edge comprising a planar spacer control end 112, a spacer insertion end 114, and a pair of spacer side edges 116. Each spacer side edge 116 spans between similar ends of the planar spacer control end 112 and spacer insertion end 114. Each side spanning between the spacer control end 112 and the spacer insertion end 114 is preferably arched outward from a center thereof. The orientation of the spacer body 102 can be referenced by the spacer control end 112, the spacer insertion end 114, a spacer upper surface 118 defining a first side thereof, and a spacer lower surface 119 defining a second, opposite side thereof.

The surgically implantable spacer 100 is segmented into an implanted spacer peripheral segment 110 and an implanted spacer inner segment 124 by a pair of segment defining slots 120. Each segment defining slot 120 is formed cutting through the spacer body 102. The segment defining slot 120 can be formed using a Wire Electric Discharge Machining (WEDM) process. It is understood that alternative cutting methods can be employed to form the segment defining slots 120. Each segment defining slot 120 spans along a longitudinal length of the spacer body 102, spanning between a location proximate the spacer control end 112 and a location proximate the spacer insertion end 114. Each segment defining slot 120 would be located between a longitudinal centerline and a peripheral edge of the spacer body 102 segmenting the spacer body 102 into the implanted spacer peripheral segment 110 and the implanted spacer inner segment 124. An optional slot stress relief 122 can be formed at each end of the segment defining slot 120 to increase the long-term reliability of the surgically implantable spacer 100. The segment defining slots 120 can be formed in any suitable shape, including linear, rectangular, arched, freeform, and the like.

A spacer control mechanism assembly receiving interface is formed in the spacer body 102. The spacer control mechanism assembly receiving interface comprises a threaded shaping passage 150, a blind receptacle 152 and a spacer control rod clearance slot 154 spanning therebetween. Each of the elements of the spacer control mechanism assembly receiving interface 150, 152, 154 are preferably provided in a linear arrangement with one another. The preferred embodiment locates the spacer control mechanism assembly receiving interface 150, 152, 154 along a longitudinal centerline of the spacer body 102. The threaded shaping passage 150 extends inward from the spacer control end 112, terminating at a threaded shaping aperture orifice 151. The blind receptacle 152 initiates at a blind receptacle orifice 153 located at a transition between the implanted spacer peripheral segment 110 and the implanted spacer inner segment 124 in a region proximate the spacer insertion end 114 and extends outward towards the spacer insertion end 114, terminating at a receptacle end wall 155. The receptacle end wall 155 is located prior to the spacer insertion end 114.

A spacer expansion control mechanism assembly 200 is provided to engage with the spacer body 102, and more specifically, the spacer control mechanism assembly receiving interface. The spacer expansion control mechanism assembly 200 comprises a spacer shaping control rod 210 extending through a spacer control sleeve 220. The spacer shaping control rod 210 is segmented into a handle portion, a spacer control rod threaded segment 216, a spacer control rod spanning segment 214, and a spacer control rod extension segment 218. The handle portion extends from a gripping end to the spacer control rod threaded segment 216. The spacer control rod threaded segment 216 is threaded to threadably engage with the threaded shaping passage 150. A spacer control rod spanning segment 214 extends from the opposite end of the spacer control rod threaded segment 216 towards an expansion end. A spacer control rod extension segment 218 is defined as a portion of the spacer shaping control rod 210 located proximate the expansion end, wherein the spacer control rod extension segment 218 is designed to be inserted into and engage with the blind receptacle 152. A spacer torsional control element 230 is affixed to an engaging end 222 of the spacer control sleeve 220. The spacer torsional control element 230 can be provided in any shape to engage with the spacer body 102. The exemplary embodiment of the spacer torsional control element 230 illustrated in the figures includes a pair of spacer torsional control sections 232, each spacer torsional control section 232 having a spacer torsional control surface 234. The spacer torsional control surface 234 engages with the exterior surfaces 118, 119 of the spacer body 102 in a manner to apply a retention torque against the rotational force generated by threading the spacer control rod threaded segment 216 into the threaded shaping passage 150. The torque can be controlled during both insertion and removal of the spacer expansion control mechanism assembly 200. Although the exemplary embodiment of the spacer torsional control element 230 includes a pair of spacer torsional control sections 232, it is understood that the spacer torsional control element 230 can be designed in any shape suitable for the application.

The spacer expansion control mechanism assembly 200 would engage with the spacer body 102 by inserting the spacer control rod extension segment 218 of the spacer shaping control rod 210 through the threaded shaping passage 150, exiting the threaded shaping aperture orifice 151, continuing within the spacer control rod clearance slot 154, passing through the blind receptacle orifice 153 and seating the spacer control rod extension segment 218 into the blind receptacle 152. As the spacer control rod extension segment 218 approaches the blind receptacle 152, the spacer control rod threaded segment 216 would engage with the threaded shaping passage 150. Upon engagement, the spacer shaping control rod 210 would be rotated to threadably engage into the threaded shaping passage 150. This threaded engagement is employed to generate an expansion force 158. The expansion force 158 extends the spacer body 102 into a planar configuration. A first end of the expansion force 158 is applied at the interface between the spacer control rod threaded segment 216 and threaded shaping passage 150. A second end of the expansion force 158 is applied at the interface between the spacer control rod extension segment 218 and blind receptacle 152.

An optional series of retention features can be integrated into the spacer body 102. The exemplary embodiment presents a variety of retention features along several edges. A first exemplary retention feature is referred to as a circumferential outer edge retention feature 130. Each of the circumferential outer edge retention features 130 extends inward from the peripheral edge of the spacer body 102. Each circumferential outer edge retention feature 130 is shaped and oriented to allow insertion of the surgically implantable spacer 100 into the joint, while restraining against a reversed movement. A second exemplary retention feature is referred to as an inner segment retention feature 140. Each of the inner segment retention features 140 extends inward from the segment defining slot 120, extending into the implanted spacer inner segment 124. Like the circumferential outer edge retention feature 130, each inner segment retention feature 140 is also shaped and oriented to allow insertion of the surgically implantable spacer 100 into the joint, while restraining against a reversed movement. A third exemplary retention feature is referred to as a circumferential inner edge retention feature 142. Each of the circumferential inner edge retention features 142 extends outward from the segment defining slot 120, extending into the implanted spacer peripheral segment 110. Like retention features 130, 140, each circumferential inner edge retention feature 142 is also shaped and oriented to allow insertion of the surgically implantable spacer 100 into the joint, while restraining against a reversed movement. In the exemplary embodiment, the retention features 130, 140, 142 are spatially arranged along each respective edge. The retention features 130, 140, 142 are preferably designed to become planar when the spacer body 102 is placed into the planar configuration and return to an angled, retention configuration when the spacer body 102 is warmed and thus returns to the undeformed configuration. Although the exemplary embodiments presented in the figures are rectangular, it is understood that the retention features 130, 140, 142 can be shaped in any suitable shape, including square, triangular, elliptical, circular, hexagonal, trapezoidal, star shaped, and the like. Although not illustration, it is also understood that the spacer body 102 can be perforated.

The spacer body 102 can be fabricated of a planar sheet of suitable material. One exemplary suitable material would be nickel titanium, also known as nitinol or any other material known to be an intermetallic compound. The composition of the alloy would be such where the transformation temperature is below a patient's common lowest temperature at the subject joint. The spacer body 102 can be shaped using any suitable metal working process known by those skilled in the art, including Wire Electric Discharge Machining (WEDM), stamping, laser cutting, machining, chemical etching, and the like. The spacer body 102 can be finished using any suitable metal finishing process known by those skilled in the art, including sanding, grinding, polishing, electro-polishing, plating, rolling, and the like to remove any imperfections created during the fabrication process. The spacer body 102 would be formed into the desired undeformed configuration using commonly known processes for forming nickel titanium or similar suitable material having a shape-memory effect. Another exemplary metal would be a gold-cadmium alloy. This classification of material is known to have a more complicated monoclinic crystal structure known as martensite at lower temperatures.

The spacer control mechanism assembly receiving interface can be formed using a drilling process. The threaded shaping passage 150 and blind receptacle 152 are formed by drilling longitudinally into the spacer body 102 from the spacer control end 112. The drilling process stops when the end of the drill bit reaches the blind receptacle end wall 155. The threaded shaping passage 150 is subsequently threaded using any commonly known tapping process. The drilling process can be used to at least partially form the spacer control rod clearance slot 154.

The features would be cut using any suitable cutting process. This can include Wire Electric Discharge Machining (WEDM), stamping, laser cutting, machining, and the like. The features can include the segment defining slots 120, the slot stress relieves 122, and the retention features 130, 140, 142, and the like. The spacer control rod clearance slot 154 can be formed by any suitable process, including laser cutting, chemical etching, machining, and the like.

The spacer body 102 can be fabricated of the following dimensions: a spacer thickness 111 can be up to 12 mm, with a preferred thickness of up to 9 mm. It is understood that the spacer thickness can be between 3 mm and 12 mm, with a preferred thickness of between 3 mm and 9 mm. The threaded shaping passage 150 can be formed having a threaded passage diameter 160 of approximately 3 mm. The threaded passage diameter 160 would be sized respective to the diameter of the spacer control rod threaded segment 216. The blind receptacle 152 can be formed having a smooth passage diameter 162 of approximately 2-2.75 mm and would also be sized respective to the diameter of the spacer control rod extension segment 218. The spacer control rod clearance slot 154 would have a depth suitable to accommodate the spacer control rod spanning segment 214 of the spacer shaping control rod 210. For example, where the spacer control rod spanning segment 214 of the spacer shaping control rod 210 has a diameter of 3 mm, the spacer control rod clearance slot 164 would have a depth of approximately 5 mm. The threaded passage diameter 160 would increase in diameter as a result of the tapping process.

Figure 10:
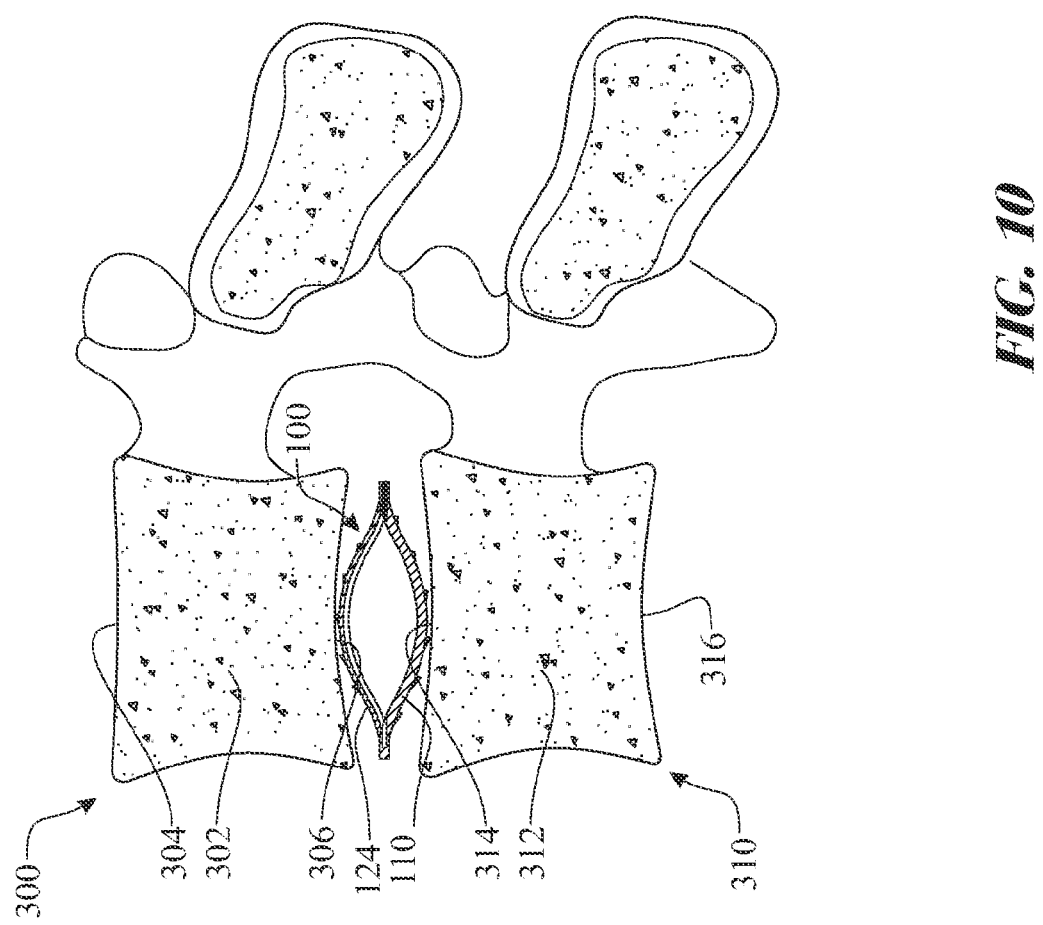
FIG. 10 presents an sectioned elevation view of the surgically implantable spacer shown in the exemplary biological application, wherein the surgically implantable spacer is shown inserted between two adjacent vertebrae.
Figure 11:
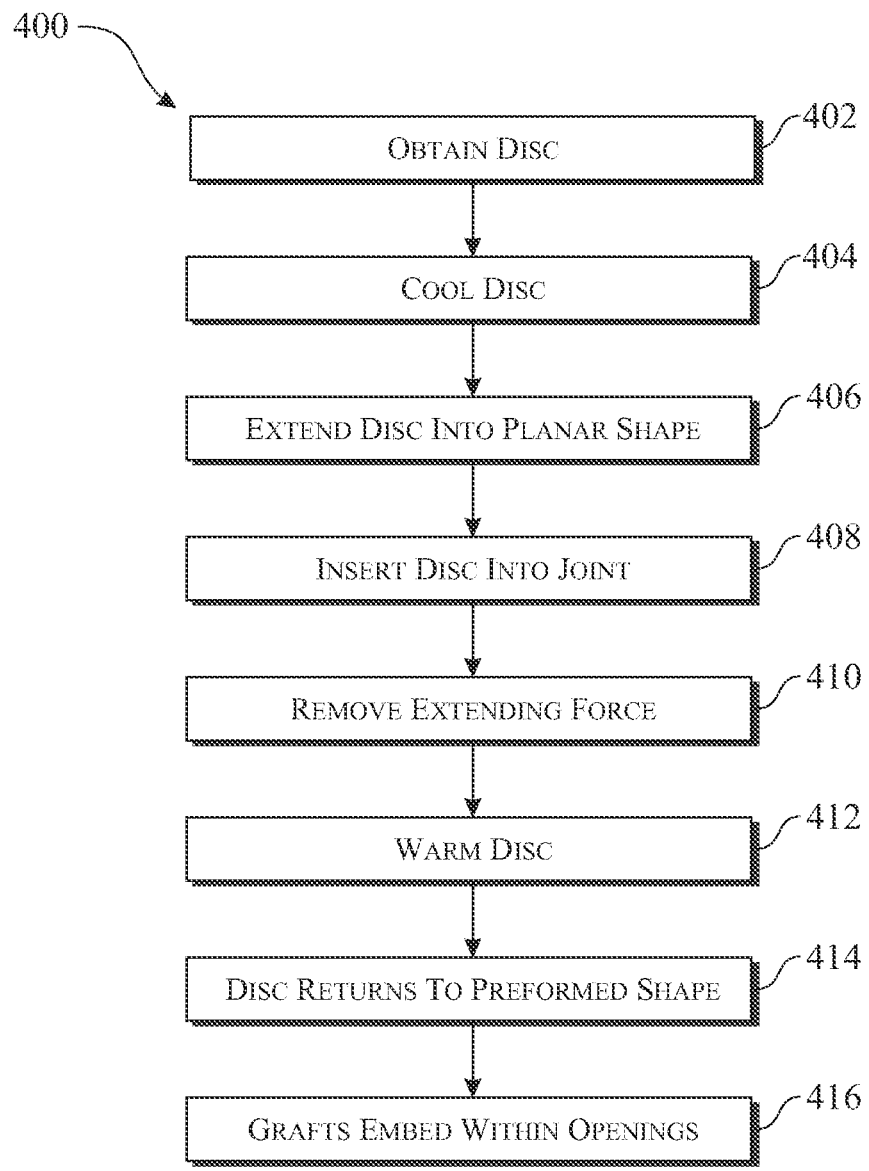
FIG. 11 presents an exemplary flow diagram describing a method of using the surgically implantable spacer.

In use, the surgically implantable spacer 100 optimizes the properties of the material. An exemplary application is presented in FIGS. 9 and 10, with FIG. 11 presenting a replacement spacer insertion process flow diagram 400 detailing the process. A first step of the replacement spacer insertion process flow diagram 400 would be to obtain a surgically implantable spacer 100 designed for the specific application (block 402). In a broadest representation, the surgically implantable spacer 100 is inserted within a joint formed between a first joint member 300 and a second joint member 310. The first joint member 300 and second joint member 310 are representative of any suitable joint.

Figure 9:
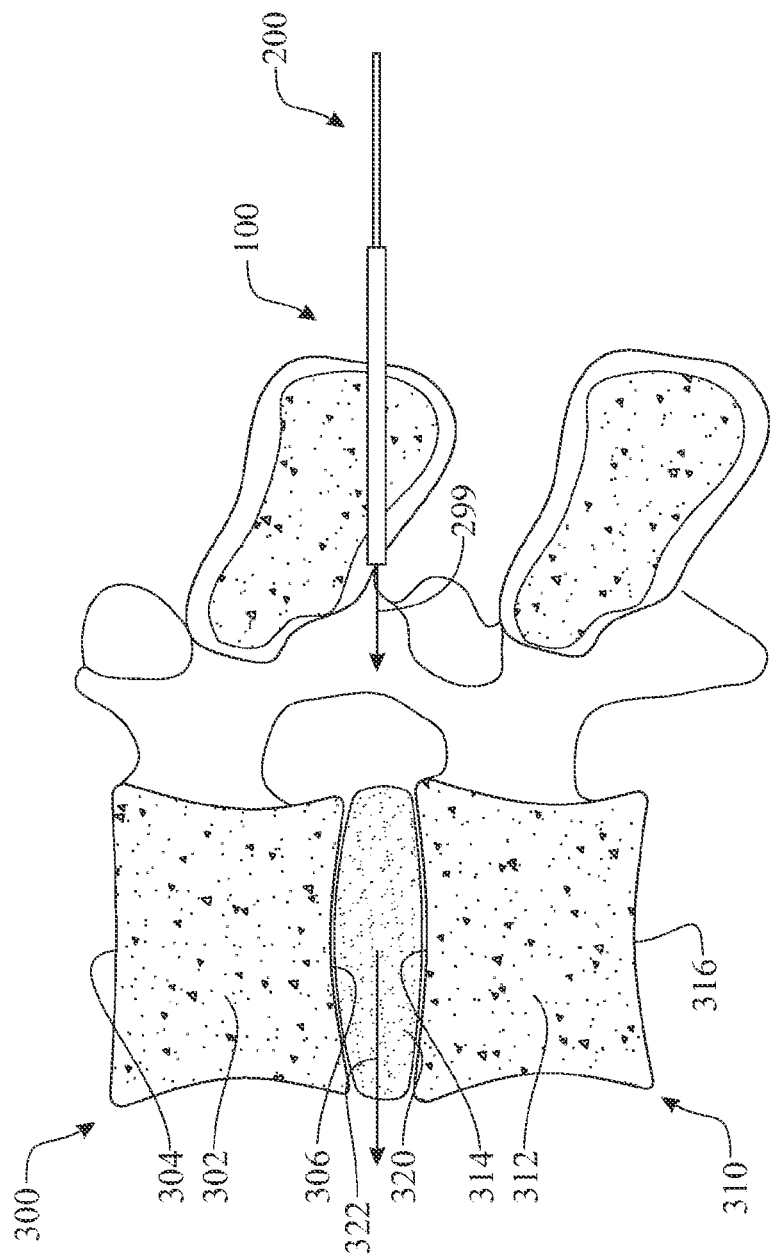
FIG. 9 presents an sectioned elevation view of the surgically implantable spacer shown in an exemplary biological application, wherein the surgically implantable spacer is shown being inserted between two adjacent vertebrae.

In the exemplary embodiment, the surgically implantable spacer 100 is designed to replace an inter-vertebrae disc 320. The intra-vertebral disc 320 would be located between two adjacent vertebrae 302, 312. Each vertebrae 302, 312 has a vertebrae first joint surface 304, 314 and a vertebrae second joint surface 306, 316. The joint surfaces can also be referred to as an end plate. The vertebrae first joint surface 314 is located adjacent to the vertebrae second joint surface 306. The intra-vertebral disc 320 is located between the vertebrae second joint surface 306 of the first vertebrae 302 and the vertebrae first joint surface 314 of the second vertebrae 312. During the insertion procedure, the intra-vertebral disc 320 is removed in accordance with an intra-vertebral disc removal 322 as illustrated in FIG. 9. Once the surgical site is readied, the surgically implantable spacer 100 is prepared for insertion (blocks 404, 406). The spacer body 102 is cooled to a temperature slightly below the transformation temperature (one suggested temperature would be below 70 degrees F.), wherein the material changes from a shape memory state to a super-elastic state (block 404). The spacer expansion control mechanism assembly 200 is assembled to the spacer control mechanism assembly receiving interface. As the spacer expansion control mechanism assembly 200 threadably engages with the threaded shaping passage 150, the spacer control rod extension segment 218 enters the blind receptacle 152. The distal end of the spacer control rod extension segment 218 eventually contacts the blind receptacle end wall 155. As the spacer expansion control mechanism assembly 200 continues to be threaded through the threaded shaping passage 150, an expansion force 158 is generated between the threaded shaping passage 150 and the blind receptacle end wall 155. The expansion force 158 extends the spacer body 102 into a planar configuration (block 406). The spacer torsional control element 230 engages with the spacer body 102 to counter any torsional forces generated by the rotational motion of the spacer shaping control rod 210 as it passes through the threaded shaping passage 150. The surgeon, assistant or both would grip the spacer control sleeve 220 and the spacer shaping control rod 210 during the extension step (block 406). Since the spacer body 102 is cooled (block 404), the material is placed into the super-elastic state. This property significantly enhances the flexibility of the material. The optional retention features 130, 140, 142 are also drawn to a planar configuration. It is noted that the optional retention features 130, 140, 142 are oriented to enable insertion even when partially or completely extended, while resisting any motion in a reverse direction. When the spacer body 102 returns to its undeformed shape, the optional retention features 130, 140, 142 are extended, wherein the optional retention features 130, 140, 142 resist motion in a reverse direction. The surgeon inserts 299 the surgically implantable spacer 100 into the subject joint, preferably using the spacer expansion control mechanism assembly 200 to aid in guiding and positioning the surgically implantable spacer 100 into the target location (block 408). It is noted that the peripheral edge extending from the spacer insertion end 114 towards the spacer control end 112 is tapered providing a lead in shape. The lead in shape aids in the insertion process. Once the surgically implantable spacer 100 is properly positioned within the joint, the surgeon removes the spacer expansion control mechanism assembly 200 from the surgically implantable spacer 100 by unthreading the spacer control rod threaded segment 216 from the threaded shaping passage 150 (block 410). During or subsequent to the removal of the spacer expansion control mechanism assembly 200 from the surgically implantable spacer 100, the spacer body 102 is warmed to a temperature slightly above the transformation temperature (block 412) (such as near 98 degrees F. or a natural internal temperature of an individual), where the spacer body 102 is returned to shape memory a shape memory state. When in the shape memory state, the spacer body 102 returns to the undeformed configuration (block 414). An optional grafting process can be utilized to accelerate a fusing process. The surgically implantable spacer 100 can be set into location by a grafting process or other similar procedure. The grafting process would place an artificial retention material or initiate a natural formation of bone or other retaining materials in adhesive or mechanical grip with features of the spacer body 102. In the exemplary embodiment, the grafting or fusing processes (block 416) can utilize the threaded shaping passage 150, the blind receptacle 152, the segment defining slots 120, the retention features 130, 140, 142, and the like to secure the spacer body 102 in position.

Although the primary application of the instant invention is directed towards an application as a spacer between adjoining bones, cartilage, and the like, it is understood that the concept of a preformed intermetallic compound can be used in other medical applications, wherein the shape changing effect can be employed to apply a tensile force between two ends thereof. The apparatus can be shaped to include a rolled end, wherein the apparatus can be cooled and straightened, affixed into the target location, then warmed, wherein the material returns to an undeformed shape, rolling or collecting the end sections or bowing the central portion, resulting in a shape that draws the ends together.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:
1. A surgically implantable spacer comprising:
a spacer member formed of a material having martensitic properties, said spacer member having an orientation reference defined by a longitudinal centerline, a lateral centerline, and a thickness;

a pair of segment defining slots formed through said spacer member, each slot routed generally parallel to said longitudinal centerline, extending from a location proximate a first end of said spacer member to a location proximate a second end of said spacer member, each slot being located between said longitudinal centerline and a respective edge of said spacer member;

said pair of slots segmenting said spacer member into at least one circumferentially located, implanted spacer peripheral segment and a centrally located implanted spacer inner segment;

a threaded shaping passage extending inward from said first spacer member end oriented along said spacer member longitudinal centerline; and a blind receptacle in linear alignment with said threaded shaping passage initiating at a blind receptacle orifice and extending towards said second spacer member end oriented along said spacer member longitudinal centerline;

wherein said spacer member is shaped into an undeformed, operating temperature configuration having said at least one implanted spacer peripheral segment forming an arch in a first direction and said implanted spacer inner segment forming an arch in a second direction, wherein said first direction is opposite of said second direction.

2. A surgically implantable spacer as recited in claim 1, wherein said spacer member material is nitinol.

3. A surgically implantable spacer as recited in claim 1, wherein each of said pair of segment defining slots is formed having an arched shape and a convex portion of said arch is proximate a circumferential edge of said spacer member.

4. A surgically implantable spacer as recited in claim 3, at least one of said pair of segment defining slots further comprising at least one inner segment retention feature integrated into an edge of said segment defining slot.

5. A surgically implantable spacer as recited in claim 3, each of said pair of segment defining slots further comprising at least one inner segment retention feature integrated into an edge of each of said segment defining slots.

6. A surgically implantable spacer as recited in claim 3, each of said pair of segment defining slots defined by a pair of edges, each segment defining slot further comprising at least one inner segment retention feature integrated into each edge of each of said segment defining slots.

7. A surgically implantable spacer as recited in claim 1, wherein said spacer member is bound by a circumferential outer edge, said spacer member further comprising at least one circumferential outer edge retention feature integrated into a portion of said spacer member proximate said circumferential outer edge.

8. A surgically implantable spacer as recited in claim 1, wherein said spacer member is bound by a circumferential outer edge, said circumferential outer edge defined by a pair of elongated segments extending between a pair of end segments, said spacer member further comprising a plurality of circumferential outer edge retention features integrated into said spacer member and spatially arranged about said elongated segments of said circumferential outer edge.

9. A surgically implantable spacer comprising:
a spacer member formed of a material having martensitic properties, said spacer member having an orientation reference defined by a longitudinal centerline, a lateral centerline, and a thickness;
a pair of segment defining slots formed through said spacer member, each slot routed generally parallel to said longitudinal centerline, extending from a location proximate a first end of said spacer member to a location proximate a second end of said spacer member, each slot being located between said longitudinal centerline and a respective edge of said spacer member;

said pair of slots segmenting said spacer member into a circumferentially located, implanted spacer peripheral segment and a centrally located implanted spacer inner segment;

a threaded shaping passage extending inward from said first spacer member end oriented along said spacer member longitudinal centerline;

a blind receptacle in linear alignment with said threaded shaping passage initiating at a blind receptacle orifice and extending towards said second spacer member end oriented along said spacer member longitudinal centerline; and at least one segment retention feature said at least one segment retention feature being at least one of:
integrated along a peripheral edge of said spacer member,
integrated along an outer edge of said segment defining slot,
integrated along an inner edge of said segment defining slot,
formed by a cut made through said spacer member and said segment retention feature being bent away from a surface of said spacer member, wherein said spacer member is shaped into an undeformed, operating temperature configuration having said at least one implanted spacer peripheral segment forming an arch in a first direction and said implanted spacer inner segment forming an arch in a second direction, wherein said first direction is opposite of said second direction.

10. A surgically implantable spacer as recited in claim 9, wherein said spacer member material is nitinol.

11. A surgically implantable spacer as recited in claim 9, wherein each of said at least one segment retention features is designed to deform into an insertion configuration when said material is cooled and return to an undeformed shape when said material returns to an operating temperature.

12. A surgically implantable spacer as recited in claim 9, wherein said spacer member is bound by a circumferential outer edge, said circumferential outer edge defined by a pair of elongated segments extending between a pair of end segments, said spacer member further comprising a plurality of circumferential outer edge retention features integrated into said spacer member and spatially arranged about said elongated segments of said circumferential outer edge.

13. A surgically implantable spacer as recited in claim 9, wherein each of said pair of segment defining slots is formed having an arched shape and a convex portion of said arch is proximate a circumferential edge of said spacer member.

14. A method of inserting a surgically implantable spacer, said method comprising steps of:
obtaining a surgically implantable spacer, said surgically implantable spacer comprising:
a spacer member formed of a material having martensitic properties, said spacer member having an orientation reference defined by a longitudinal centerline, a lateral centerline, and a thickness,
a pair of segment defining slots formed through said spacer member, each slot routed generally parallel to said longitudinal centerline, extending from a location proximate a first end of said spacer member to a location proximate a second end of said spacer member, each slot being located between said longitudinal centerline and a respective edge of said spacer member, said pair of slots segmenting said spacer member into at least one circumferentially located, implanted spacer peripheral segment and a centrally located implanted spacer inner segment, a threaded shaping passage extending inward from said first spacer member end oriented along said spacer member longitudinal centerline, and a blind receptacle in linear alignment with said threaded shaping passage initiating at a blind receptacle orifice and extending towards said second spacer member end oriented along said spacer member longitudinal centerline, wherein said spacer member is shaped into an undeformed, operating temperature configuration having said at least one implanted spacer peripheral segment forming an arch in a first direction and said implanted spacer inner segment forming an arch in a second direction, wherein said first direction is opposite of said second direction;

reducing a temperature of said surgically implantable spacer to a temperature below said transformation temperature wherein said material becomes super-elastic;

extending said surgically implantable spacer into a planar shape by applying an extending force to said surgically implantable spacer;

inserting said surgically implantable spacer into a biological joint;

removing said extending force from said surgically implantable spacer; and warming said spacer to a temperature above said transformation temperature, wherein said material returns to its undeformed, operating temperature configuration.

15. A method of inserting a surgically implantable spacer as recited in claim 14, the method comprising additional steps of:

applying said extending force to said surgically implantable spacer by inserting a spacer shaping control rod through said threaded shaping passage of a spacer body of said surgically implantable spacer, wherein said threaded shaping passage is located at said first spacer member end;

seating a distal end of said spacer shaping control rod into said blind receptacle of said spacer member, wherein said blind receptacle is located at said second spacer member end, wherein said first end and said second end are located at opposite ends of said spacer;

engaging a spacer control rod threaded segment of said spacer shaping control rod with said threaded shaping passage; and rotating said spacer shaping control rod to drive said spacer shaping control rod inward causing separation between said first spacer member end and second spacer member end.

16. A method of inserting a surgically implantable spacer as recited in claim 14, the method comprising an additional step of:

inserting said surgically implantable spacer between two members of a biological joint.

17. A method of inserting a surgically implantable spacer as recited in claim 14, the method comprising an additional step of:

removing said spacer shaping control rod from said spacer member;

warming said inserted surgically implantable spacer, wherein said warmed inserted surgically implantable spacer returns to said undeformed, operating temperature configuration.

18. A method of inserting a surgically implantable spacer as recited in claim 17, the method comprising an additional step of:

retaining a rotational orientation of said spacer member by engaging a spacer torsional control element with said spacer member.

19. A method of inserting a surgically implantable spacer as recited in claim 14, the method comprising an additional step of:

retaining a spacer body of said spacer member within said biological joint by integrating at least one retention feature along at least one of:

a circumferential edge of said spacer member, an outer edge of at least one of said pair of segment defining slots, and an inner edge of at least one of said pair of segment defining slots.

20. A method of inserting a surgically implantable spacer as recited in claim 14, the method comprising an additional step of:

forming at least one retention feature within a spacer body of said spacer member by utilizing said martensitic properties of said spacer member.

* * * * *